United States Patent [19]

Berg

[11] Patent Number: 5,443,697

[45] Date of Patent: Aug. 22, 1995

[54] SEPARATION OF HEPTANE FROM 1-HEPTENE BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 246,151

[22] Filed: May 19, 1994

[51] Int. Cl.⁶ .......................... B01D 3/40; C07C 7/08
[52] U.S. Cl. .......................... 203/57; 203/60; 203/62; 203/63; 203/65; 585/857; 585/862; 585/864; 585/866
[58] Field of Search .......................... 203/62, 63, 60, 57, 203/65; 585/856, 857, 862, 864, 866

[56] References Cited

U.S. PATENT DOCUMENTS

| | | | |
|---|---|---|---|
| 2,461,993 | 2/1949 | McKinnis | 203/62 |
| 3,087,866 | 4/1963 | Burch | 203/6 |
| 3,388,531 | 6/1968 | Bolles et al. | 203/57 |
| 5,032,232 | 7/1991 | Lee et al. | 203/64 |
| 5,068,011 | 11/1991 | Lee et al. | 203/58 |
| 5,085,740 | 2/1992 | Lee et al. | 203/64 |
| 5,085,741 | 2/1992 | Brown et al. | 203/68 |
| 5,100,515 | 3/1992 | Lee et al. | 203/63 |
| 5,277,766 | 1/1994 | Berg | 203/57 |

*Primary Examiner*—Wilbur Bascomb, Jr.

[57] ABSTRACT

Heptane is difficult to separate from 1-heptene by conventional distillation or rectification because of the proximity of their boiling points. Heptane can be readily separated from 1-heptene by extractive distillation. Effective agents are diacetone alcohol, ethyl butyrate and dimethylsulfoxide.

2 Claims, No Drawings

SEPARATION OF HEPTANE FROM 1-HEPTENE BY EXTRACTIVE DISTILLATION

FIELD OF THE INVENTION

This invention relates to a method for separating heptane from 1-heptene using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

There are a number of commercial processes which produce mixtures of hydrocarbons that boil very close together, e.g. petroleum refining and Fischer-Tropsch. Two close boiling compounds frequently produced are heptane, B.P.=98° C. and 1-heptene, B.P.=94° C. The relative volatility between these two is 1.10 which makes it virtually impossible to separate them by conventional rectification. Extractive distillation would be an attractive method of effecting the separation of heptane from 1-heptene if agents can be found that (1) will create a large apparent relative volatility between heptane and 1-heptene , and (2) are easy to recover from heptane or 1-heptene. Table 1 shows the relative volatility required to obtain 99% purity. With no agent, the relative volatility is 1.10 and 129 actual plates are required. With an agent giving a relative volatility of 2.1, only 17 actual plates are required.

OBJECTIVE OF THE INVENTION

The object of this invention is to provide a process or method of extractive distillation that will enhance the relative volatility of heptane from 1-heptene or 1-heptene from heptane in their separation in a rectification column. It is a further object of this invention to identify organic compounds which in addition to the above constraints, are stable, and can be separated from heptane or 1-heptene and recycled to the extractive distillation column with little decomposition.

TABLE 1

Theoretical and Actual Plates Required vs. Relative Volatility for 1-Heptene - Heptane Separation

| Relative Volatility | Theoretical Plates Required At Total Reflux, 99% Purity | Actual Plate Required 75% Efficiency |
|---|---|---|
| 1.10 | 97 | 129 |
| 1.3 | 35 | 47 |
| 1.6 | 20 | 27 |
| 2.1 | 13 | 17 |

SUMMARY OF THE INVENTION

The objects of this invention are provided by a process for the separation 1-heptene from heptane which entails the use of certain organic compounds when employed as the agent in extractive distillation.

TABLE 2

Effective Extractive Distillation Agents For Separating Heptane From 1-Heptene

| Compounds | Relative Volatility |
|---|---|
| None | 1.10 |
| Diacetone alcohol | 1.45* |
| 5-Methyl-2-hexanone | 1.3 |
| Amyl acetate | 1.3* |
| Ethyl butyrate | 2.1 |
| Acetophenone | 1.25* |
| Dimethylsulfoxide | 1.58* |
| Dimethylacetamide | 1.35* |
| Dinonyl phenol | 1.35 |

*Brings heptane out as overhead

DETAILED DESCRIPTION OF THE INVENTION

I have discovered that certain organic compounds will greatly improve the relative volatility of 1-heptene from heptane and permit the separation of 1-heptene from heptane by rectification when employed as the agent in extractive distillation. Table 2 lists the compounds that I have found to be effective. They are diacetone alcohol, 5-methyl-2-hexanone, amyl acetate, ethyl butyrate, acetophenone, dimethylsulfoxide, dimethylacetamide and dinonyl phenol.

THE USEFULNESS OF THE INVENTION

The usefulness or utility of this invention can be demonstrated by referring to the data presented in Tables 1 and 2. All of the successful agents show that heptane can be separated from 1-heptene by means of extractive distillation in a rectification column and that the ease of separation as measured by relative volatility is considerable.

WORKING EXAMPLES

EXAMPLE 1

Sixty grams of heptane, 20 grams of 1-heptene and 40 grams of diacetone alcohol were charged to a vapor-liquid equilibrium still and refluxed for five hours. Analysis indicated a vapor composition of 87.6% heptane, 12.4% 1-heptene; a liquid composition of 82.8% heptane, 17.2% 1-heptene. This is a relative volatility of 1.45.

EXAMPLE 2

A solution comprising 135 grams of heptane and 15 grams of 1-heptene was placed in the stillpot of a 5.5 theoretical plate glass perforated plate rectification on column. When refluxing began, an extractive agent comprising dimethylsulfoxide was pumped into the top of the column at a rate of 15 ml/min. The temperature of the extractive agent as it entered the column was 75° C. After establishing the feed rate of the extractive agent, the heat input to the heptane-1-heptene in the stillpot was adjusted to give a total reflux rate of 40 ml/min. After two hours of operation, overhead and bottoms samples were collected and analysed by gas chromatography. The overhead composition was 98.7% heptane, 1.3% 1-heptene and the bottoms composition was 85.8% heptane, 14.2% 1-heptene. This gives a relative volatility of 1.58 for each theoretical plate.

EXAMPLE 3

Sixty-five grams of heptane, fifteen grams of 1-heptene and 40 grams of ethyl butyrate were charged to the vapor-liquid equilibrium still and refluxed for four hours. Analysis indicated a vapor composition of 24.4% 1-heptene, 75.6% heptane; a liquid composition of 13.2% 1-heptene, 86.8% heptane. This is a relative volatility of 2.1.

I claim:

1. A method for recovering heptane from a mixture of heptane and 1-heptene which comprises distilling a mixture of heptane and 1-heptene in the presence of from one to five parts by weight of an extractive agent per part of heptane-1-heptene mixture, recovering the heptane as overhead product and obtaining the 1-heptene and the extractive agent as bottoms product, wherein said extractive agent consists of one material selected from the group consisting of diacetone alcohol, amyl acetate, acetophenone and dimethylsulfoxide.

2. A method for recovering 1-heptene from a mixture of 1-heptene and heptane which comprises distilling a mixture of 1-heptene and heptane in the presence of from one to five parts by weight of an extractive agent per part of 1-heptene-heptane mixture, recovering the 1-heptene as overhead product and obtaining the heptane and the extractive agent as bottoms product, wherein said extractive agent consists of one material selected from the group consisting of 5-methyl-2-hexanone and dinonyl phenol.

* * * * *